US00PP18554P2

(12) United States Plant Patent
Carruth

(10) Patent No.: US PP18,554 P2
(45) Date of Patent: Mar. 4, 2008

(54) GRANDIFLORA ROSE PLANT NAMED 'WEKISOSBLIP'

(50) Latin Name: *Rosa hybrida*
Varietal Denomination: WEKisosblip

(75) Inventor: Thomas F. Carruth, Altadena, CA (US)

(73) Assignee: Weeks Wholesale Rose Grower, Inc., Upland, CA (US)

( * ) Notice: Subject to any disclaimer, the term of this patent is extended or adjusted under 35 U.S.C. 154(b) by 0 days.

(21) Appl. No.: 11/594,665

(22) Filed: Nov. 6, 2006

(51) Int. Cl.
*A01H 5/00* (2006.01)

(52) U.S. Cl. ..... Plt./132; Plt./131

(58) Field of Classification Search ..... Plt./132, Plt./131
See application file for complete search history.

(56) References Cited

U.S. PATENT DOCUMENTS

PP4,012 P * 1/1977 Bailey ..... Plt./132
PP10,948 P * 6/1999 Meilland ..... Plt./131
PP13,449 P2 * 1/2003 Carruth ..... Plt./102

* cited by examiner

*Primary Examiner*—Wendy Haas
(74) *Attorney, Agent, or Firm*—Christie, Parker & Hale, LLP

(57) ABSTRACT

A new variety of Grandiflora rose suitable for garden decoration, having flowers of red-purple with a lavender eye coloration.

1 Drawing Sheet

Classification:
The present invention relates to a new *Rosa hybrida* plant.
Variety denomination:
The new plant has the varietal denomination 'WEKisosblip'.

BACKGROUND OF THE INVENTION

This invention relates to a new and distinct variety of Grandiflora Rose. It has an undisseminated seedling of my creation as its seed parent with the following genetic origin ('International Herald Tribune'×Rosa soulieana derivative)×('Sweet Chariot'×'Blue Nile') and has an undisseminated seedling of my creation as its pollen parent with the following genetic origin 'Blueberry Hill'×'Stephen's Big Purple'.

SUMMARY OF THE INVENTION

Among the features which distinguish the new variety from other presently available and commercial rose cultivars known to the inventor are the following combination of characteristics: its many stipitate glands and hairs on the peduncle, its red suffusion on the inside of the sepals, its moderately undulated petals, its strong fruity citrus-like to spicy fragrance and its unique red-purple with a lavender eye flower coloration. The plant has an upright somewhat spreading growing habit, suitable for outdoor garden decoration.

Asexual reproduction of the new variety by budding as performed in Kern County and Upland, Calif., shows that the foregoing and other distinguishing characteristics come true to form and are established and transmitted through succeeding asexual propagations. 'WEKisosblip' may be asexually propagated by cuttings, budding and grafting. The budding and grafting successfully occurred on the plant/rootstock *Rosa hybrida* cv. 'Dr. Huey' (unpatented).

COMPARISON WITH PARENTS

The new rose may be distinguished from its seed parent, an undisseminated seedling of my creation by the following combination of characteristics: whereas 'WEKisosblip' bears double flowers (about 25 to 38 petals) of red-purple with a lavender eye coloration, the undisseminated seedling bears flowers of an even purply-red coloration with significantly lesser petalage. The new variety is classified as a grandiflora rose with an upright somewhat spreading medium height growing habit (about 110 to about 130 cm. in height), whereas the seed parent is classified as a floribunda rose with a more compact rounded significantly shorter growing habit.

The new variety may be distinguished from its pollen parent, an undisseminated seedling of my creation by the following combination of characteristics: whereas 'WEKisosblip' bears medium sized flowers (about 6.7 to about 10.0 cm. in diameter) of red-purple with a lavender eye coloration, the undisseminated seedling bears significantly smaller flowers (about 5.5 to about 8.1 cm. in diameter) of lavender coloration. The new variety bears moderately glossy foliage, whereas the pollen parent bears matte foliage.

COMPARISON WITH THE CLOSEST COMMERCIALLY AVAILABLE CULTIVAR

The new variety may be distinguished from its closest commercially available cultivar, 'WEKstephitsu' (U.S Plant Pat. No. 13,449) by the following combination of charactersitics: whereas 'WEKisosblip' bears medium sized flowers (about 6.7 to about 10.0 cm. in diameter) of red-purple with a lavender eye coloration, 'WEKstephitsu' bears significantly smaller flowers (about 6.2 to about 8.3 cm. in diameter) of magenta to lavender-blue coloration. The new variety bears double flowers (about 25 to 38 petals), whereas the closest commercially available cultivar bears fully double flowers with significantly heavier petalage (about 41 to about 53 petals).

BRIEF DESCRIPTION OF ILLUSTRATION

The accompanying photograph illustrates the new variety and shows the flowering thereof from bud to full bloom depicted in color as nearly correct as it is possible to make in a color illustration of the character. Throughout this specification, color references and/or values are based upon the Colour Chart to The Royal Horticultural Society (1966) except where common terms of color definition are employed.

DESCRIPTION OF THE NEW VARIETY

The following description is of 3 to 4 year-old rose plants of the new variety grown outdoors in Upland, Calif. in the month of October. Phenotypic expression may vary with environmental, cultural and climatic conditions, as well as differences in conditions of light and soil.

FLOWER

The new variety sometimes bears its flowers singly, usually in clusters of two to six or more per stem. Flowers may be borne in regular rounded clusters on strong short to long stems (about 21 to about 85 cm.). Outdoors, the plant blooms abundantly and nearly continuously during the growing season. The flowers have a strong fruity cirtus-like to spicy fragrance.

BUD

The peduncle is about 3.2 to about 5.1 cm. in length, of average caliper (about 0.2 to about 0.3 cm. in diameter), and usually erect. It is moderately smooth, with many stipitate glands and hairs. Peduncle color is between 146C and 148B often heavily suffused, especially on the side exposed to the sun, with between 183B and 187A.

Before the calyx breaks, the bud is about 1.0 to about 1.7 cm. in diameter at the widest point, about 1.4 to about 1.9 cm. in length, and pointed to somewhat ovoid in shape. The surface of the bud bears some long foliaceous appendages, very few stipitate glands and some hairs, usually with slender mostly entire to sometime much cut foliaceous parts extending beyond the tip of the bud about ½ or more of its length. Bud color is between 144A and 146B often lightly suffused, especially on the side exposed to the sun, with between 183B and 187A.

The sepals are about 1.7 to about 3.5 cm. in length and about 0.7 to about 1.0 cm. in width at the widest point. The outer surface color of the sepal is between 144A and 146B often lightly suffused, especially on the side exposed to the sun, with between 183B and 187A. The inner surface color of the sepal is between 137A and 138B. After the sepals open, the inner surface color is often heavily suffused, especially on the area exposed to the sun, with between 187A and 187B. The inner surface is covered with fine wooly tomentum; sepal margins are lined with many stipitate and hairs.

The receptacle of the flower is of somewhat short length (about 0.5 to about 0.7 cm.) and average in caliper (about 0.8 about 1.0 cm. in diameter). The receptacle is moderately globular to somewhat rounded in form. Its surface is smooth with some hairs and with thick fleshy walls. The receptacle color is between 144A and 146B.

As the petals open (after the calyx breaks), the bud is about 1.5 to about 2.6 cm. in diameter at the widest point, about 1.7 to about 2.8 cm. in length, and moderately ovoid to somewhat globular in form. The color of the under surfaces of the newly opened petals is between 59A and 61A. At the point where the petal attaches, there is a small zone of between 1D and 154D. The color of the upper surfaces of the newly opened petals is between 80C and 82C at the lower third of the petal gradually suffusing to between 187B and 59A toward the remaining surface of the petal. At the point where the petal attaches, there is a small zone of between 1D and 154D.

BLOOM

When fully open, the bloom ranges from about 6.7 to about 10.0 cm. in diameter. Petalage is double with about 25 to 38 petals and about 4 to 8 petaloids irregularly arranged. When partially open, the bloom form is globular to moderately cupped, and the petals are loosely spiraled to somewhat cupped with petal edges somewhat reflexed outward. When fully open, the bloom form is more cupped and the petals are loosely cupped to moderately undulated with petal edges moderately reflexed outward and inward.

PETALS

The substance of the petals is moderately heavy to somewhat crisp and of medium to slightly thick thickness, with upper surfaces moderately satiny to somewhat shiny and under surfaces moderately shiny. The petals are about 3.3 to about 4.7 cm. in length and about 2.3 to about 4.1 cm. in width at the widest point. Petal margins are entire.

The outer petals are broadly obovate in shape with rounded apices.

The inner petals are moderately oblanceolate in shape with rounded apices.

Petaloids are about 1.5 to about 3.7 cm. in length and about 0.9 to about 2.7 cm. in width at the widest point. Petaloids are irregularly shaped somewhat oblanceolate to oblong with rounded apices.

NEWLY OPENED FLOWER

The under surface color of the outer, intermediate and inner petals is between 72B and 77B along the central vein at the center of the petal suffusing to between 60B and 59B toward the edges. At the point where the petal attaches, there is a small zone of near 2D surrounded by a large zone of between 155A and 155C. The upper surface color of the outer, intermediate and inner petals is between 76C and 76D at the lower third of the petal gradually suffusing to between 61A and 71B toward the remaining surface of the petal. At the point where the petal attaches, there is a small zone of near 2D.

The under and upper surface color of the petaloids are similar in coloration to the upper and under surfaces of the outer, intermediate and inner petals.

The general tonality of the newly opened flower is between 76C and 76D at the center of the flower gradually suffusing to between 61A and 71B toward the outside of the flower.

THREE-DAY-OLD FLOWER

The under surface color of the outer, intermediate and inner petals is between 81C and 80C sometimes lightly blushed toward the edge of the petal with near 71B. At the point where the petal attaches, there is a very large zone of between 155A and 155C. The upper surface color of the outer, intermediate and inner petals is between 85D and 155D at the lower third of the petal gradually suffusing to between 72B and 71C toward the remaining surface of the petal. There is no visible change in coloration at the point where the petal attaches.

The under and upper surface color of the petaloids are similar in coloration to the upper and under surfaces of the outer, intermediate and inner petals.

The general tonality of the three-day-old flower is between 85D and 155D at the center of the flower gradually suffusing to between 72B and 71C toward the outside of the flower.

On the spent bloom, the petals usually drop off cleanly.

In October in Upland, Calif., blooms on the bush growing outdoors generally last about four to five days. Cut roses from plants grown outdoors and kept at normal indoor living temperatures generally last about four to five days.

MALE REPRODUCTIVE ORGANS

Stamens are many in number (average about 154) and are arranged regularly about the pistils; a few are mixed with petaloids. The filaments are of somewhat long length (about 0.5 to about 1.3 cm.) most with anthers. Filaments are between 4C and 5D in color sometimes very lightly suffused with near 53C. The anthers are somewhat small to medium for the class and all open approximately at the same time. Anther color is between 23B and 16C when immature and between 200C and 161C at maturity. Pollen is very abundant and between 15B and 16A in color.

FEMALE REPRODUCTIVE ORGANS

Pistils vary in number (average about 125). The styles are moderately even, somewhat short in length (about 0.3 to about 0.6 cm.), thin in caliper and loosely bunched to somewhat columnar. Stigma color is between 16D and 14D. Style color is between 53A and 60A. Ovaries are all enclosed in the calyx.

Hips are of moderately short length (about 1.0 to about 1.5 cm.), rounded to moderately globular in form and between 28B and 30B in color when ripe. The hip surface is very smooth with few hairs and with thick fleshy walls. The sepals are moderately permanent and usually straight in shape.

The seeds are irregularly rounded, smooth in texture, approximately 6 to about 14 per hip, about 0.3 to about 0.6 cm. in diameter at the widest point and between 161B and 162C in color.

FOLIAGE

The compound leaves are usually comprised of three to seven leaflets and are borne in moderate quantities. The five-leaflet leaves are about 9.3 to about 12.5 cm. in length and about 7.2 to about 9.6 cm. in width at the widest point, crisp to somewhat leathery in texture and moderately glossy in finish. The terminal leaflets are about 3.4 to about 5.8 cm. in length and about 2.4 to about 4.1 cm. in width at the widest point, shaped moderately ovate to somewhat oval with acute to somewhat acuminate apices and rounded to slightly acute bases. Their margins are usually simply serrate.

The upper surface color of the mature leaf is between 147A and 137A. The under surface color of the mature leaf is between 137C and 146C. The upper surface color of the young leaf is between 146A and 146B, usually heavily suffused with between 187A and 183A mostly on the very edge and on the central vein of the leaf. The under surface color of the young leaf is between 143C and 146B, usually heavily suffused with between 187B and 183A.

The rachis is moderately light in caliper and somewhat rough. The upper side is shallowly grooved with few hairs and some stipitate glands on the edges of the grooves. The under side of the rachis is somewhat rough with few stipitate glands and small prickles. The rachis color is near 145A on the under side and near 137A on the upper side, often heavily suffused on the young leaves with between 187A and 183A.

The stipules are about 1.3 to about 1.8 cm. in length and of medium width (about 0.4 to about 0.6 cm.) with moderately long straight points that usually turn out at an angle of more than 45 degrees and sometimes recurve toward the stem. The stipules color is between 145A and 137C often moderately suffused on the young leaves with between 187B and 183B.

The petiole is moderately light in caliper and somewhat rough. The upper side is shallowly grooved with few hairs and some stipitate glands on the edges of the grooves. The under side of the petiole is somewhat rough with few stipitate glands and small prickles. The petiole is about 0.6 to about 1.5 cm. in length and about 0.1 to about 0.2 cm in diameter at the widest point. The petiole color is near 145A on the under side and near 137A on the upper side, often heavily suffused on the young leaves with between 187A and 183A.

The plant displays an average degree of resistance to powdery mildew and rust as compared to other commercial varieties grown under comparable conditions in Upland, Calif. The plant's winter hardiness and drought/heat tolerance are yet to be determined.

GROWTH

The plant has an upright somewhat spreading medium height growing habit (about 110 to about 130 cm. in height and about 56 to about 75 cm. spread at the widest point), with full branching. It displays moderately vigorous growth and the canes are of medium caliper for the class.

The color of the major stems is between 146C and 147B. They bear some large prickles that are about 0.6 to about 0.9 cm. in length. The large prickles are almost straight and angled slightly downward with a medium length somewhat narrow oval base; prickle color is between 165C and 165A. The major stem bears very few small prickels.

The color of the branches is between 146D and 146C. They bear some large prickles which are of similar size and shape to the large prickles on the major stems; prickle color is between 160B and 162C sometimes moderately suffused with 187C and 183D. The branches bear few small prickles of similar shape and coloration.

The color of the new shoots is between 146B and 146C often heavily suffused with between 187A and 183A. They bear many large prickles which are of similar size and shape to the large prickles on the major stems; prickle color is between 145A and 144B usually heavily suffused with between 187A and 187B. The shoots bear few small prickles of similar shape and coloration.

What is claimed is:

1. A new and distinct Grandiflora rose plant of the variety substantially as described and illustrated herein.

* * * * *

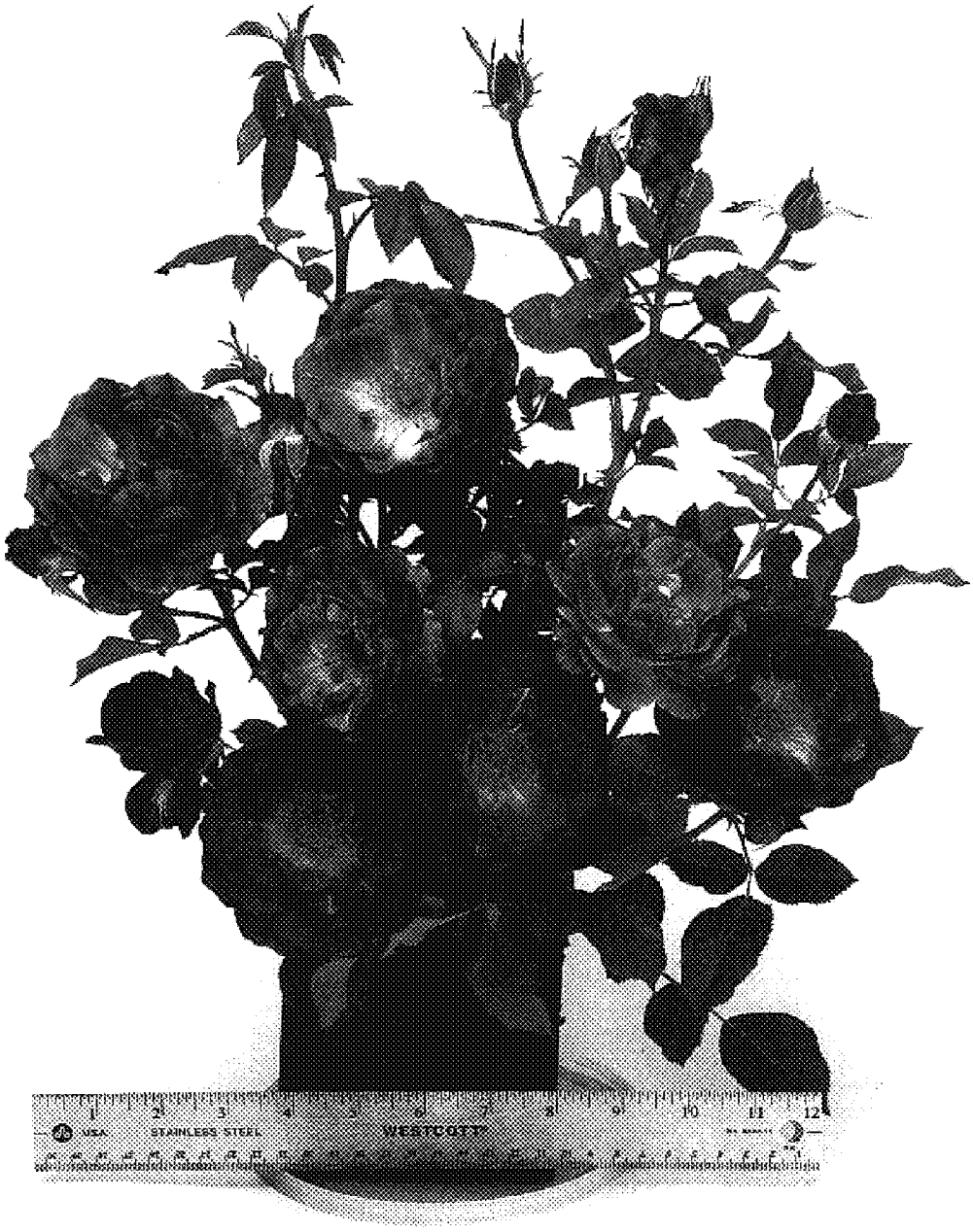
STAINLESS STEEL
WESTCOTT